United States Patent [19] [11] 3,969,540
Jensen [45] July 13, 1976

[54] ENZYMATICALLY PREPARED METAL PROTEINATES

[75] Inventor: Ned L. Jensen, Layton, Utah

[73] Assignee: Albion Laboratories, Inc., Clearfield, Utah

[22] Filed: Sept. 11, 1975

[21] Appl. No.: 612,371

[52] U.S. Cl. .............................. 426/657; 195/28 R; 195/29; 195/30; 426/648
[51] Int. Cl.² ............................................ A23J 1/02
[58] Field of Search ............. 260/112 R; 195/29, 30, 195/28; 426/271, 56, 657, 648

[56] References Cited
UNITED STATES PATENTS

| | | | |
|---|---|---|---|
| 3,396,104 | 8/1968 | Miller | 260/112 R |
| 3,775,132 | 11/1973 | Richards | 426/56 |
| 3,857,966 | 12/1974 | Feldman et al. | 426/56 |

*Primary Examiner*—A. Louis Monacell
*Assistant Examiner*—Robert J. Warden
*Attorney, Agent, or Firm*—Criddle, Thorpe & Western

[57] ABSTRACT

A method of preparing metal proteinates from natural proteinacous material without destroying naturally occurring vitamins and hormones which comprises neutralizing a protein containing material, subjecting said material to enzymatic hydrolysis, adjusting the enzymatically digested hydrolysate to a slightly basic pH and adding a metal salt thereto to form a metal proteinate precipitate. The proteinate thus formed is a chelate of polypeptides with metals and is substantially free from metal salts and single amino acid proteinates.

4 Claims, No Drawings

ENZYMATICALLY PREPARED METAL PROTEINATES

BACKGROUND OF THE INVENTION

This invention relates to a process of enzymatically preparing metal proteinates and the products obtained therefrom. More specifically, this invention relates to enzymatically prepared metal proteinates wherein the proteinate is a chelate of an enzymatically digested protein with bivalent essential metal wherein the naturally occurring vitamins and hormones in the protein are not destroyed.

Heretofore the hydrolysis of proteinaceous material to form metal chelates or proteinates has utilized sufficiently strong acidic and basic reaction conditions which require the use of special equipment. Such hydrolysis results in the destruction of some of the essential amino acids forming the proteinaceous material. For example, U.S. Pat. No. 3,396,104 teaches a process whereby proteinaceous materials are subjected to a basic hydrolysis at a pH between about 8 and 10.5 and thereafter subjected to an acid hydrolysis with phosphoric acid or other strong acid in the presence of a metal salt to form a chelated amino acid complex. Similarly, U.S. Pat. No. 3,775,132 teaches a method for the production of metal proteinates wherein the proteinaceous material is first hydrolyzed by a base-acid-base hydrolysis prior to mixing with the metal salt to form the metal proteinate precipitate. These patents are disadvantageous in that hydrolysis with either acids or bases requires relatively high temperatures. Since proteins are made up from a combination of amino acids, some of the naturally occurring amino acids in the proteinaceous substances are destroyed. For example, tryptophan is destroyed in acid hydrolysis. Serine, threonine, tyrosine and several others are partially destroyed in basic hydrolysis. Not only are certain amino acids destroyed in the acid or base hydrolysis process, but also naturally occurring vitamins and hormones, which may be beneficial when ingested into the animal body, are also destroyed.

It is therefore an object of the present invention to prepare metal proteinates by the enzymatic digestion of proteinaceous material whereby naturally occurring amino acids are not destroyed.

It is a further object of the present invention to prepare metal proteinates under mild reaction conditions whereby the naturally occurring vitamins and hormones in the proteinaceous material are not destroyed.

A still further object of the present invention is to prepare metal proteinates prepared from enzymatically digested proteinaceous material whereby the hydrolysate consists of polypeptides, but wherein the hydrolysis is not carried out to the point that single amino acids are formed.

These and other objects may be accomplished by means of a novel digestion and chelation process wherein vitamins and hormones are not destroyed and no amino acids are formed under the mild conditions utilized. This leaves the proteinaceous substance in a naturally digested form which is the form that an animal body prefers. Natural digestion in the body is done by two enzymes, pepsin and pancreatin, which leaves the protein in the polypeptide form.

A particular advantage of the present invention is that the enzymatic digestion allows the formation of a substrate of mineral and protein, i.e., a metal proteinate which is essentially salt free. Most hydrolysis processes use an acid followed with a base for neutralizing. Upon spray drying these form a product, which is between 50% and 70% salt. In the present process, the filtration of the enzymatically digested metal proteinate from the water gives a metal proteinate which is essentially salt free.

Another advantage of the present invention is that in enzymatic hydrolysis, polypeptides are produced as a substrate for the chelation process. No acids or bases are used for hydrolysis, therefore no amino acids forming the polypeptides are destroyed and the hydrolysis is sufficiently mild that no single amino acid is formed.

As utilized in the present application, the term metal proteinate has reference to a metal chelate wherein a protein hydrolysate is used as the ligand thereby forming a polycyclic complex with a biologically essential bivalent metal. The coordination complex is formed between the bivalent metal and at least two polypeptide ligands, depending upon the mineral involved. For example, zinc forms $Sp_3$ orbital hybrids in aqueous solution. This means that two polypeptide residues will chelate with zinc to form the metal proteinate. The planes of the polypeptide residue are at right angles to each other forming a tetrahedral complex. They are attached in two places to the zinc atom forming a polycylic chelated complex. Iron, on the other hand, forms octahedral complexes with three polypeptide residues. Each mineral therefore has its characteristic configuration for forming complexes depending on the oxidation state. They may have different ligands and form different configurations. Biologically essential metals which may be utilized include iron, copper, zinc, manganese, cobalt, chromium, calcium, magnesium and vanadium.

In order for chelation to take place it is essential that both the enzymatically produced protein hydrolysate and the complexing metal be in solution. The metals are therefore added in the form of soluble inorganic salts.

The protein hydrolysate is formed under mild conditions which do not result in the complete hydrolysis of the protein to the individual amino acid state, and which also does not destroy other beneficial substances in the protein such as vitamins and hormones.

The enzymatic hydrolysis is brought about by placing a comminuted protein source in an aqueous solution. In general, the solution will contain about 20% by weight/volume of proteinaceous material to water. Preferred sources of protein include naturally occurring tissues such as muscle, heart, liver, brain, pancreas, spleen, kidneys, duodenum, thymus, and orchic. As stated, these tissues can be used as carrier materials for minerals without destroying the valuable vitamins and hormones which may be destroyed by treatment with acids, bases or heat. Other protein sources such as casein, gelatin, collagen or albumin may be used.

Any protease may be utilized as the enzyme. Typical of such proteases are pepsin, pancreatin, trypsin, papain, bacterial protease and fungal protease. The enzyme is added in an amount of about 1 to 10 percent by weight based on the protein.

The hydrolysis is carried out at between about 25° and 70° C. so that none of the amino acids in the polypeptides are destroyed in the hydrolysis process. The hydrolysis period may last anywhere from a matter of hours to a matter of weeks depending upon the amount of hydrolysate to be formed and the ease of hydrolysis. In general, the hydrolysis will be carried out over a period of about 2 hours to about 5 days. Preferably, the hydrolysis is carried out under neutral conditions and it may be necessary to adjust the pH of the protein-enzyme digestion solution by the use of an acid or base. Small amounts of acids or bases such as hydrochloric acid and sodium hydroxide may be utilized to neutralize the enzymatic hydrolysis mixture, but not in amounts sufficient to cause acid or base hydrolysis. If desired, a small amount of preservative such as toluene may also be present during the digestion or hydrolysis process.

As the proteinaceous material is hydrolyzed into polypeptides it will be brought into solution. Preferably the hydrolysis is brought about by constantly stirring the mixture and maintaining the temperature relatively constant.

At the end of the digestion period the mixture may, if desired, be brought to a boil for a short period of time to kill the enzyme so that further hydrolysis will not take place. However, this tends to destroy natural materials such as vitamins and hormones. The solubilized hydrolysate may then be directly treated with a soluble metal salt to form a metal proteinate or may first be filtered to separate the hydrolysate from undigested tissue.

Since protein hydrolysates are chains of amino acids, it is evident that these substances will contain charged groups. The extent of such charged groups will vary with the pH and the titration curve of a protein hydrolysate will represent the composite of the effects of the various groups as they are able to combine with acids and bases. For example, in polypeptides, the charged groups may be due to amino groups belonging to the N-terminal amino acid of each polypeptide chain, or to carboxyl groups belonging to the C-terminal amino acid of a polypeptide chain. A consequence of charged groups in protein hydrolysates is the ability of the hydrolysate to form complexes with other compounds. In order to form a true metal proteinate (chelate) one must have the proper amount of constituents at the right conditions. It is essential that the mineral and protein hydrolysate both be in soluble form. It is also important that the protons be removed from the carboxyl groups before a chemical bond with the mineral can be formed. In the case of protein hydrolysates, both the amino and carboxyl functions must be free from interfering protons in order for chelation to take place. With protein hydrolysates, such as polypeptides, most protons remain intact in neutral solutions and therefore the pH is preferably adjusted in a range more basic than a pH of 7.5. Preferably the pH will be adjusted to a point that is on the alkaline side of the isoelectric point. In general, pHs of about 7.5 to 10 are preferred. Since the hydrolysate has previously been formed, the pH adjustment does not materially affect the stability of the hormones and vitamins in the protein hydrolysate. The appropriate amount of metal salt is added to an aqueous solution of the protein hydrolysate to form a precipitate which is filtered and then washed. The amount of metal salt that is added is adjusted such that there are at least 2 moles of protein hydrolysate or polypeptide per mole of metal salt. Otherwise, a true chelate will not be formed. The metal chelates readily precipitate, and unlike the protein hydrolysates, do not have a net charge. In other words, there are no free ions associated with the metal proteinates.

The product thus obtained can be dried and mixed in appropriate amounts as a dietary supplement in the form of a powder, tablet, liquid or in any other form desired, and then administered to an animal having a need for the particular metal proteinate thus formed, or if desired the metal proteinates may be mixed in an appropriate base for topical or cosmetic application.

It becomes at once apparent that many different metal proteinates can be formed according to the present invention and that the particular metals used can be used in predetermined amounts. The Amount and source of proteinaceous material enzymatically digested can be predetermined so that the vitamins and hormones which will be present in the final product can also be predicted. A distinct advantage of the present invention is that the metals, vitamins and hormones are delivered to the body utilizing a proteinaceous substrate in a naturally digested form which is the form most readily accepted and assimilated by the body.

The following examples are illustrative of, but are not limitations upon the present invention.

EXAMPLE 1

Into a 300 gallon jacketed tank equipped with a stirrer and a temperature controller was placed 1000 pounds of water. While stirring, 200 pounds of casein was added. Six pounds of sodium hydroxide was added to neutralize and solubilize the acid casein. To this mixture was added a mixture of enzymes as follows: 3 pounds of papain, 3 pounds of bacterial protease, and 3 pounds of fungal protease. 20 pounds of toluene was added as a preservative. The mixture was covered and stirred for a period of 4 days at a temperature of 50°C. The pH was then adjusted to 8.5 with sodium hydroxide and the mixture was brought to a boil for about 15 minutes to kill the enzymatic action. The hydrolysate thus obtained was filtered while hot through muslin. To the filtrate thus obtained was added 33 pounds of zinc chloride whereupon a precipitate was formed, which, when washed and dried, consisted of about 200 pounds of zinc proteinate containing 8% by weight zinc.

EXAMPLE 2

The hydrolysis procedure of Example 1 was followed and to the filtered protein hydrolysate solution was added 75 pounds of ferrous sulfate ($FeSO_4.7H_2O$). Upon washing and drying there was collected about 175 pounds of an iron proteinate containing 9% by weight iron.

EXAMPLE 3

Again following the procedure of Example 1 there was added to the filtered protein hydrolysate solution 41 pounds of cupric chloride ($CuCl_2.2H_2O$) along with 1000 pounds of methyl alcohol. The precipitate formed was collected and dried and consisted of about 180 pounds of copper proteinate containing 11% by weight copper.

EXAMPLE 4

The procedure of Example 1 was again repeated and to the filtered protein hydrolysate solution was added 56 pounds of manganese chloride ($MnCl_2.4H_2O$). The precipitated protein was collected and dried and consisted of about 170 pounds of manganese proteinate containing 9% by weight manganese.

EXAMPLE 5

Into 200 pounds of water was placed 200 pounds of lypholyzed liver powder and 6 pounds of sodium hydroxide to neutralize the solution. To the above mixture was added 1 pound each of papain, bacterial protease, and fungal protease. Twenty pounds of toluene was added as a preservative. The mixture was covered and allowed to digest with stirring at room temperature overnight. The following morning 75 pounds of ferrous sulfate ($FeSO_4.7H_2O$) was added and the solution was neutralized to a pH of 8.5 with sodium hydroxide. The iron proteinate thus obtained contained the natural ingredients found in the liver powder prior to the enzymatic hydrolyzation. The proteinate thus obtained contained about 12% by weight iron.

EXAMPLE 6

To 200 pounds of water was added 200 pounds of raw gland tissue. The tissue was a mixture of brain, liver, spleen, kidney, pancreas, duodenum, and heart. To this mixture was added 1 pound each of papain, bacterial protease, and fungal protease. Twenty pounds of toluene was added as a preservative. The mixture was covered and allowed to stir overnight at ambient temperatures. The following morning a mixture of metal salts as given in the following table was added:

| | | |
|---|---|---|
| $MgCl_2.6H_2O$ | 12% Mg | 83 pounds |
| $FeSO_4.7H_2O$ | 20% Fe | 30 pounds |
| $ZnCl_2$ | 47% Zn | 12.8 pounds |
| $MnCl_2.4H_2O$ | 27% Mn | 3.7 pounds |
| $CuCl_2.2H_2O$ | 37% Cu | 2.7 pounds |
| $CrCl_3.6H_2O$ | 19% Cr | 48 grams |
| $H_2MoO_4$ | 53% Mo | 19 grams |

The pH of the mixture was adjusted with sodium hydroxide to about 8.5, and the resulting slurry consisting of a mixture of metal proteinates and unhydrolyzed raw gland tissue was taken up on 200 pounds of isolated soy protein and dried at a low temperature. The naturally occurring vitamins, hormones and other ingredients in the raw gland tissue was unchanged. However, the metal was firmly incorporated into the tissues in the form of metal proteinates having a mineral content of about 11% by weight.

EXAMPLE 7

Into a container was added 200 pounds of water and 200 pounds of autolyzed primary grown yeast. To this mixture was added 1 pound each of papain, bacterial protease, and fungal protease. Again, twenty pounds of toluene was added as a preservative. The mixture was allowed to stir overnight at room temperature and the following morning sufficient sodium hydroxide was added to adjust the pH to 8.5. This procedure was repeated with 4 different yeast solutions. To the first solution was added 33 pounds of zinc chloride, to the second solution was added 75 pounds of ferrous sulfate ($FeSO_4.7H_2O$), to the third solution was added 41 pounds of cupric chloride ($CuCl_2.2H_2O$), and to the fourth solution was added 56 pounds of manganese chloride ($MnCl_2.4H_2O$). Upon the addition of the metal salt a precipitate was formed. The unhydrolyzed yeast and metal proteinate thus produced were taken up on 200 pounds of isolated soy protein and dried at a temperature of between about 50° and 60°C. Upon analysis it was shown that each metal had been chelated into the yeast, but that the yeast still maintained the high vitamin content as primary grown yeast. The metal contents ranged from about 9 to 14% by weight and the metal proteinate recovery varied from about 175 to 200 pounds.

EXAMPLE 8

Into a ribbon blender was placed 180 pounds of water and 2 pounds of bacterial protease. The mixture was stirred and heated to 55°C. Isolated soy protein was added to the mixture 10 pounds at a time until 80 pounds had been added over a period of one hour. The mixture was allowed to digest or hydrolyze for one additional hour and then 280 pounds of anhydrous calcium chloride was added and the mixture was again stirred for 30 minutes. To this mixture was added 90 pounds of isolated soy protein and 20 pounds of micro cell E. The mixture was stirred for an additional 5 minutes and then put on trays to dry at 75°C. The product consisted of partially hydrolyzed soy protein containing calcium proteinate firmly intermixed therewith.

EXAMPLE 9

The procedure of Example 8 was followed with the exception that 300 pounds of manganese chloride ($MgCl_2.12H_2O$) was substituted for the calcium chloride.

EXAMPLE 10

Into a tank was placed 450 pounds of water and the water was heated to 55°C. To the water was added 350 grams of Bromelain. While stirring, 400 pounds of gelatin were added to this mixture, 100 pounds at a time, at intervals of 20 minutes. At the end of two hours, the mixture was brought to a boil for 10 minutes to stop the enzyme. To this mixture was added 66 pounds of zinc chloride and the pH was adjusted to about 8.5 with sodium hydroxide to form a precipitate. The mixture, consisting of zinc proteinate, was taken up with 500 pounds of isolated soy protein and dried at 70 °C.

EXAMPLE 11

The procedure of Example 10 was followed with the exception that 350 grams of papain was utilized as the enzyme.

EXAMPLE 12

A mixture was formed by adding 1000 pounds of water to a tank with 10 pounds of sodium hydroxide and 200 pounds of casein. To this mixture was added 3 pounds of pancreatin as an enzyme and 20 pounds of toluene as a preservative. The mixture was stirred and digested at 37°C. for a period of two days. At that time the pH of the mixture was adjusted to a pH of 2 with hydrochloric acid and 3 pounds of pepsin was added along with additional toluene. This mixture was stirred for two more days to allow further digestion to take place. Following this the mixture was adjusted to a pH of 8.5 and 45 pounds of zinc chloride were added. A precipitate was formed consisting of a zinc proteinate. The mixture was filtered on muslin and dried.

I claim:
1. A composition of matter comprising naturally occurring proteinaceous tissues selected from the group consisting of muscle, heart, liver, thymus, brain, spleen, kidneys, duodenum, pancrease, and orchic a portion of which have been enzymatically hydrolyzed by a protease to produce polypeptides; said polypeptides being chelated with bivalent biologically essential metals to form metal proteinates.
2. A composition of matter according to claim 1 wherein the naturally occurring vitamins and hormones have not been destroyed by the hydrolysis process and remain intact.
3. A composition of matter according to claim 2 wherein the bivalent biologically essential metals are selected from the group consisting of iron, copper, zinc, manganese, cobalt, chromium, calcium, magnesium and vanadium.
4. The composition of matter claimed in claim 3 wherein the metal proteinate is essentially salt free.

* * * * *